United States Patent [19]

Cambio, Jr.

[11] Patent Number: 4,662,868
[45] Date of Patent: May 5, 1987

[54] SYRINGE APPARATUS AND VALVE EMPLOYED THEREIN

[75] Inventor: Orlando D. Cambio, Jr., Bristol, Wis.

[73] Assignee: University of Pittsburgh, Pittsburgh, Pa.

[21] Appl. No.: 759,331

[22] Filed: Jul. 26, 1985

[51] Int. Cl.⁴ .............................................. A61M 1/00
[52] U.S. Cl. ....................................................... 604/32
[58] Field of Search ...................... 604/27, 30, 32, 37, 604/38, 48, 73, 236, 238, 248; 222/484–486; 215/313; 137/625.11, 625.46; 285/DIG. 7, 330

[56] References Cited

U.S. PATENT DOCUMENTS

| 2,485,842 | 10/1949 | Pennington | 604/248 |
| 3,618,637 | 11/1971 | Santomieri | 604/248 |
| 4,082,095 | 4/1978 | Mendelson et al. | 604/32 |
| 4,187,849 | 2/1980 | Stim | 604/248 |

FOREIGN PATENT DOCUMENTS 771968 4/1957 United Kingdom ......... 285/DIG. 7

Primary Examiner—C. Fred Rosenbaum
Assistant Examiner—J. L. Kruter
Attorney, Agent, or Firm—Thomas H. Murray; Clifford A. Poff

[57] ABSTRACT

A syringe assembly includes a syringe receiving a plunger at one end and at the other end there is an extended part which can be heat deformed to hold a ported cap member and a rotatable valve member to the syringe. The ported cap member includes ports adapted to be connected to tubes for receiving, or conveying fluid material. The ported cap member has a central opening through which the extended part extends. The rotatable valve member is located between the syringe and the ported cap member for sealingly engaging both the syringe and the ported cap member by O-ring seals therebetween. The ported cap member is non-rotatably connected to the syringe by a splined connection.

23 Claims, 13 Drawing Figures

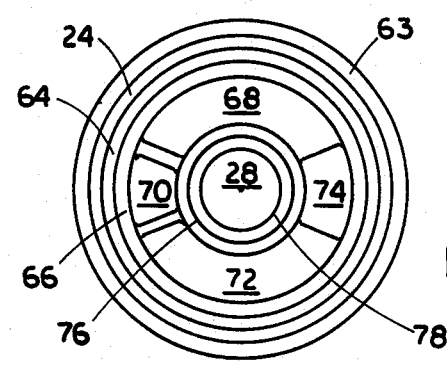
FIG. 7
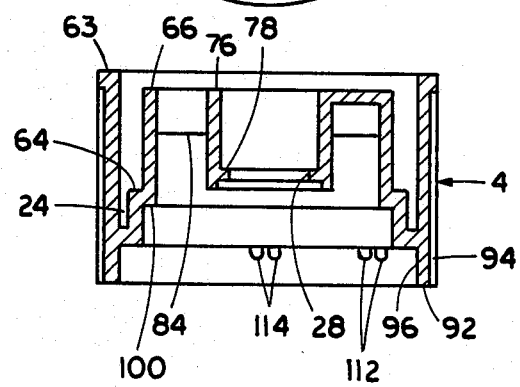
FIG. 8
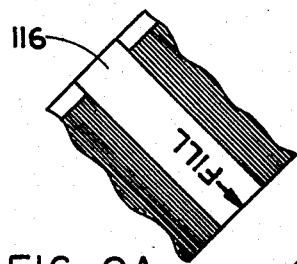
FIG. 9A
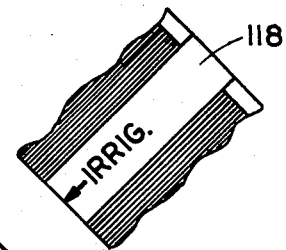
FIG. 9B
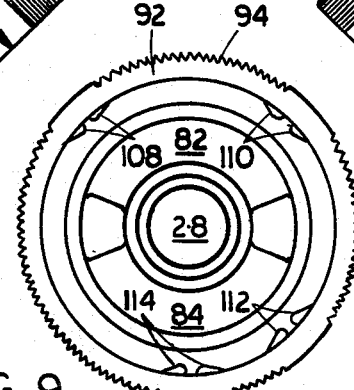
FIG. 9
FIG. 9C
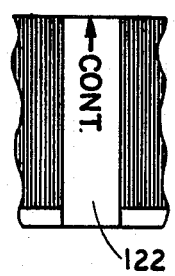
FIG. 9D

SYRINGE APPARATUS AND VALVE EMPLOYED THEREIN

BACKGROUND OF THE INVENTION

1. Field of the Invention

This invention relates to assembly for introducing fluid into and removing liquid from a cavity, chamber or an organ, particularly a cavity or organ of the body of a biological being, such as a body of a human or animal, for example, the abdominal cavity or stomach or bladder. In particular it relates to a rotary valve means for use in a closed system wherein a sealed connection is maintained with all of various fluid supply and/or drain lines. The valve means permits the installation and evacuation of fluid in a closed system by prohibiting contamination of fluid within the system by a contaminating medium outside the system. In certain fields of use, the invention can be used to eliminate risk of infection. The assembly is especially compact and convenient to use.

2. Description of the Prior Art

Some examples of devices for introducing fluid into an organ of the body of an animal (e.g., the stomach or the bladder) and removing fluid from same are shown in U.S. Pat. Nos. 2,564,977; 3,048,192; 3,157,201; 3,780,736; 3,834,372; 3,990,447; and 4,082,095.

At one time, there was in this art the problem that the system was "open" rather than "closed" i.e., that it was not possible to maintain a closed system which would ensure the sterility of liquid drawn from a closed, sterile source and introduced into the body of an animal, particularly a human. It is, of course, highly desirable, in connection with any procedure of introducing liquid into and removing liquid from a human organ (such as the bladder or stomach or heart) that conditions be maintained such that a sterile liquid is introduced and to the extent possible remains sterile, since the patient otherwise faces a risk of incurring an infection by a pathogenic agent, which infection will add to and complicate a pre-existing condition.

In connection with the art of supplying liquids to and withdrawing liquid from the human bladder, it is known from the Vega U.S. Pat. No. 3,990,447, that such supply and withdrawal of liquid may be accomplished in a closed system the use of apparatus disclosed therein.

The above-mentioned Vega patent discloses a unitary means which has lines or branches which make sealed connections with all of the four following things: (1) a liquid supply, (2) a syringe, (3) a catheter leading to the bladder, and (4) a drain line. Individual manually operable clamps are associated with each line or branch for shutting it off. This system solves the problem of how to supply liquid under sterile conditions in a closed system. However, the possibility of operator error exists when manipulating the various clamps and the use of a multitude of individual clamps has a tendency to cause the device to become cumbersome and bulky to the patient.

The above-mentioned Vega patent discloses one form of unitary rotary multiposition valve as does Mendelson Pat. No. 4,082,095. However, both of these provide that the syringe and the port connections must rotate relative to one another for the valving function. Thus, twisting of the lines or syringe disorientates the assembly from the operator's established perspective. In the Mendelson U.S. Pat. No. 4,082,095 there is a stomach pump which contains a syringe and an adjustable valve means as a unit. The valve construction uses a radial channel to permit the flow of fluid always between the syringe and any one of the tubes connected to the valve, thus precluding fluid flow between the tubes only. This renders the valve and syringe unit unusable for many medical applications such as continuous irrigation with intermittent forced infusion (e.g., for breaking up blood clots or other obstructions). It is known to use a valve to control fluid flow in a system including a syringe from, for example, Murphy U.S. Pat. No. 3,048,192; Littermann U.S. Pat. No. 3,157,201; Chen U.S. Pat. No. 3,780,736 and Turney U.S. Pat. No. 3,834,372. However, the valve in each of these systems is not an integral part of the syringe but comprises a separate component part of the system. The requirement to assemble the system from the numerous component parts gives rise to the need for a compact valving arrangement integrated with a fluid container such as a syringe.

SUMMARY OF THE INVENTION

It is an object of the present invention to provide a fluid control system integrated with a fluid container in a manner to form a compact unit which can be operated without permitting the entry of contaminates into an otherwise closed fluid system and/or without twisting the fluid lines and container relative to one another.

It is a further object of the present invention to provide a fluid control system having an elongated container used to support a valve which can be rotated to selectively establish flow paths between a plurality of fluid lines and when desired, isolate the container from the fluid lines.

According to the present invention, there is provided an assembly including a container, a ported cap member having ports adapted to be connected to means for receiving, or conveying fluid material, a rotatable valve member between the container and the ported cap member sealed in a fluid-tight manner with both the container and the cap member, and means for interlocking the ported cap member in a fixed manner with the container.

In its preferred form the container of the assembly includes a syringe having at the end thereof remote from a plunger handle a generally centrally disposed shaft member forming an extended part of the syringe, over which there are fitted first the rotatable valve member and then, nested within the rotatable valve member, the ported cap member which is suitably fixed as by splines or keys so as to be non-rotatable with respect to the shaft. Thus, the ported cap, rotatable valve member and container are coaxially arranged along an axis extending lengthwise of the shaft. The rotatable valve member has, in its face toward the ported cap member a groove for receiving the ported cap member and a set of compartments such that different ones of the ports may be caused to communicate with each other or be shut off or be caused to communicate with the syringe through an eccentrically located hole in an end face of the container which is directed toward the valve. Desirably, means are provided so that the operator will know in which one, of a plurality of possible positions, the valve is in at any given moment. Such means may comprise indicia on the syringe and the exterior of the rotatable valve member, or suitable protuberances and detents so that the rotatable valve member is yieldingly held against rotation in one of the desired positions, and the operator is able to sense tactilely that a particular position has been obtained. The yieldable arrangement between the protuberances and detents may produce an audible click when each position is attained.

DESCRIPTION OF THE DRAWINGS

A complete understanding of the invention may be obtained from the foregoing and following description thereof, taken in conjunction with the appended drawings, in which:

FIG. 7 is a top plan view of the rotatable valve member shown in FIG. 1;

FIG. 8 is an elevational view, in section, of the rotatable valve member shown in FIG. 7; and FIG. 9 is a bottom plan view of the rotatable valve member shown in FIG. 7 and including auxiliary portions, FIGS. 9A, 9B, 9C, and 9D, which are partial side views of the exterior of the rotatable valve member, showing indicia thereon.

DESCRIPTION OF THE PREFERRED EMBODIMENTS

Figure 1:
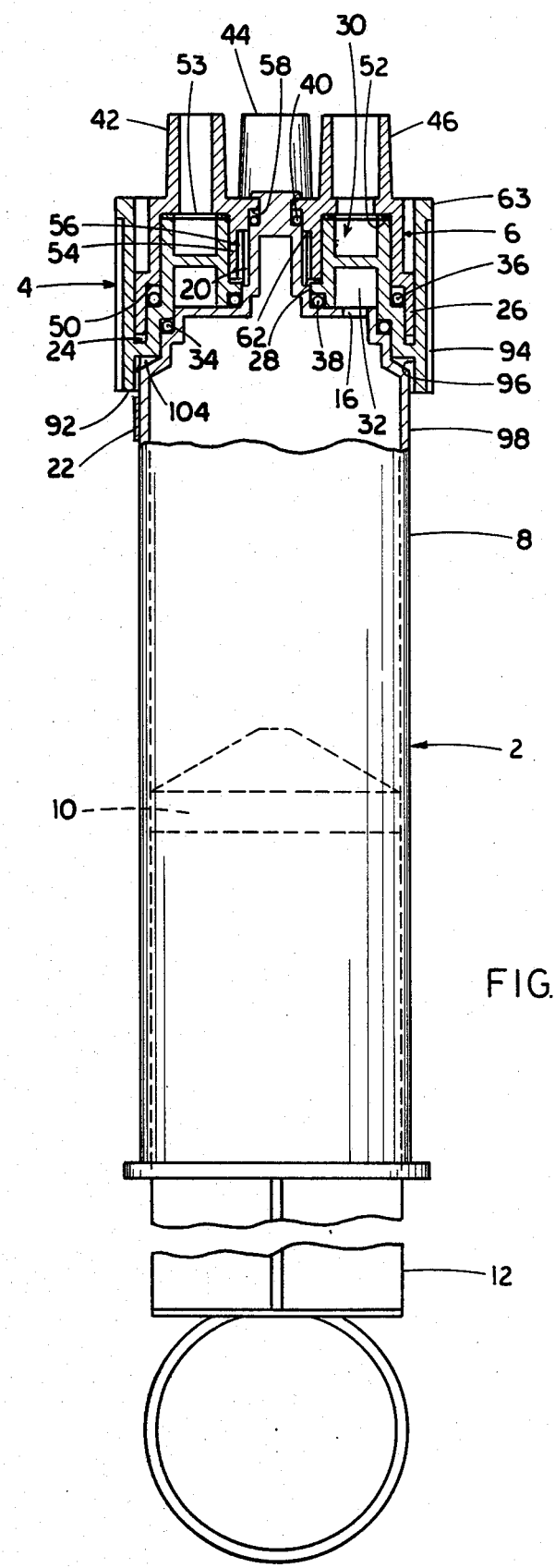
FIG. 1 is a sectional view showing the assembly of a ported cap member, rotatable valve member, and a container embodied as a syringe in accordance with the present invention.
Figure 4:
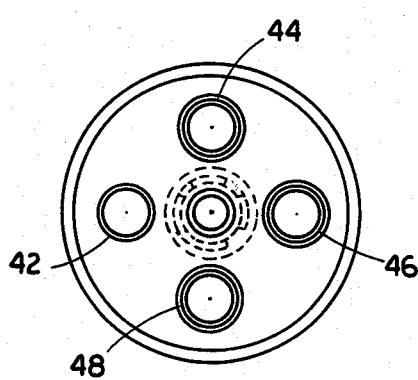
FIGS. 4, 5, and 6 are, respectively, a top plan view, an elevation, and a bottom plan view of the ported cap member shown in FIG. 1.
Figure 2:
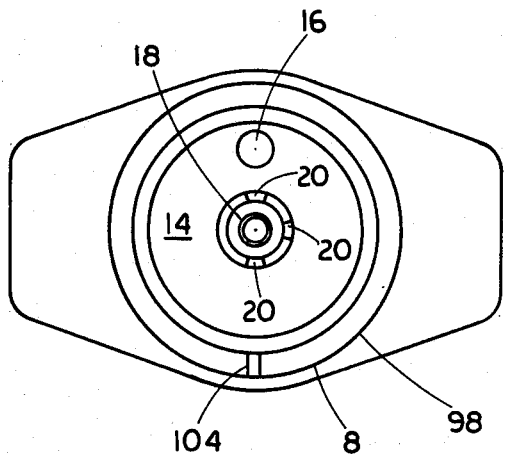
FIGS. 2 and 3 are a plan view and an elevational view, respectively, of the syringe means shown in FIG. 1.
Figure 5:
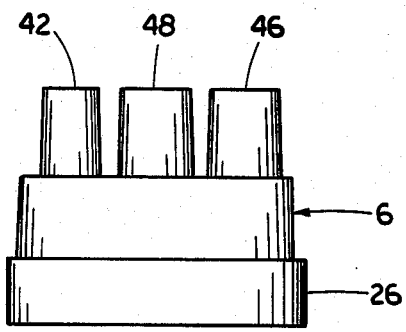
Figure 6:
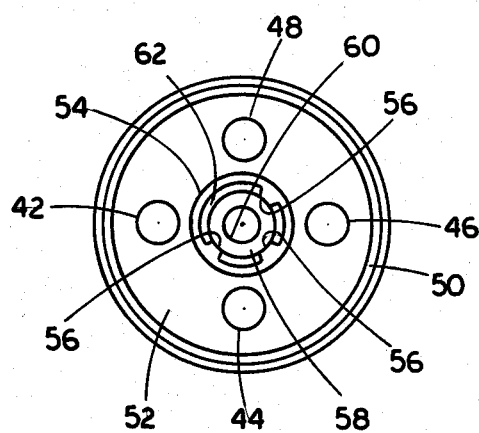
Figure 3:
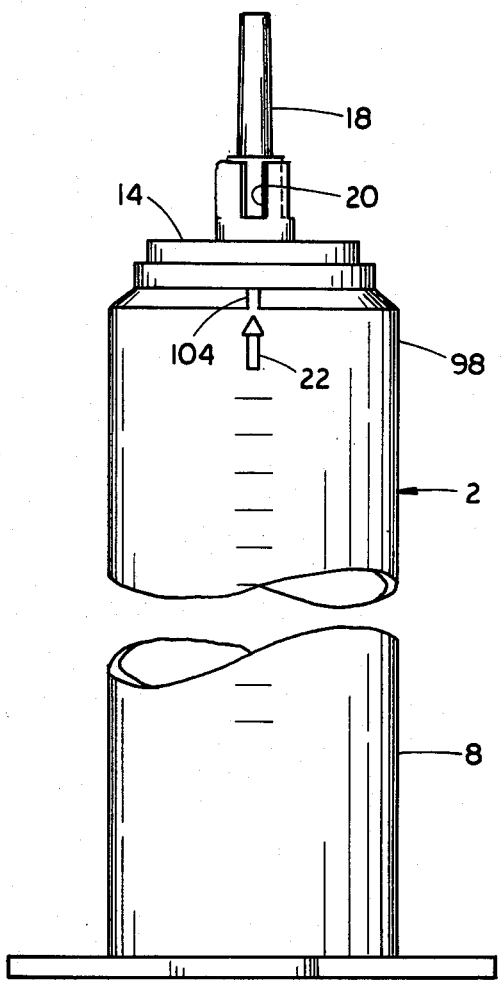

Referring to FIG. 1, there are shown, respectively, from bottom to top, a container embodied as a syringe assembly generally indicated at 2, a rotatable valve member generally indicated at 4, and a fixed ported cap member, generally indicated at 6. The syringe member 2 consists of a generally cylindrical shell 8, within which there is fitted a plunger 10 having a handle 12. In the end of the syringe member 2 remote from the handle 12 and plunger 10, there is a face 14, which has therein an eccentrically located hole 16. For reasons which will become apparent in connection the further description of this embodiment of the invention, the syringe member 2 has an exterior configuration which is such that it may be closely contacted by the rotatable valve member 4. Moreover, the syringe assembly further preferably integrally contains a central shaft member 18. This shaft member 18 can be a separate element carried by the syringe. Key slots 20, for purposes hereinafter to be described, are formed on the shaft member 18. Member 18 is elongated to such an extent so as to extend through the rotatable valve member 4 and the ported cap member 6. Valve member 4 rotates about an axis generally corresponding to a central axis extending along shaft member 18 and centrally along the extended length of the cylindrical shaft 8 of syringe member 2. Shaft member 18 can, if desired, be an independent arbor secured to the ported cap member and connected in a suitable socket on the end face of the syringe. The syringe assembly 2 preferably includes, in its exterior, a suitable indicia, such as the arrow 22 as well as transverse graduate markings to indicate the volume of fluid in the syringe (FIG. 3).

Referring now to the rotatable valve member 4, it will be seen that it has, in its face toward ported cap member 6, a groove 24 which, it will be understood, is circular and capable of receiving the part 26 of the ported cap member 6. The rotatable valve member 4 contains a region, indicated at 28, which is in the nature of a central opening of such size as to permit the passage therethrough of the shaft member 18 connected to the syringe assembly 2.

The side or face of the rotatable valve member 4 towards the ported cap member 6 also contains, between the central opening 28 and the groove 24, an area 30 which serves various purposes, such as permitting various ones of the ports on the ported cap member 6 to communicate with one another or be shut off, or communicate with the chamber 32 which exists between the rotatable valve member 4 and the syringe member 2.

In accordance with the present invention, in having the rotatable valve member 4 fit in a satisfactory and leak-proof manner with both the syringe assembly 2, on the one hand, and the ported cap member 6, on the other hand, there are preferably provided, as shown, four O-ring members 34, 36, 38, and 40, which are positioned, respectively, as shown in FIG. 1. These O-rings seals 34, 36, 38, and 40 may be made of any suitably resilient material, such as rubber or plastic. All of the O-rings seal radially as shown in FIG. 1. The O-rings are compressed between an inside and outside diameter. O-rings 34 and 38 are also under axial loading after assembly. By this design, a constant thrust loading of the rotatable valve member is maintained against the face surface 52. O-rings 36 and 40 are under no axial loading.

The ported cap member 6 shown more particularly in FIGS. 1 and 4-6 inclusive, is nested in the valve member by proving an annular rim 26 which is adapted to fit within the groove 24 of the rotatable valve member 4. Cap member 6 also comprises a plurality of ports 42, 44, 46, and 48, which are adapted to be connected, as known to those skilled in the art, with various lines for conveying fluid so as to form a closed system.

In FIG. 1, it can be seen that there exists a shoulder 50, immediately adjacent to the interior of the rim 26, adapted to contain the O-ring seal 36. The numeral 52 designates the generally circular interior face surface of the ported cap member 6 on which there is placed a gasket 53 comprised of any medically acceptable material to form a fluid seal for preventing port-to-port leakage between the cap member 6 and the rotating valve member 4. As can be seen from FIGS. 1 and 6, the ported cap member 6 has, rising from the face surface 52, a collar 54 which has, in the embodiment shown, three inwardly extending keys or splines 56, adapted to interfit with the key slots 20 on the syringe so as to prevent relative rotation between these members. By this construction and relationship of parts, fluid lines extending from the cap member will not become twisted when operating the valve member. Also, the operator will not become disorientated to indicia on the syringe because there is no need to rotate the syringe. The keys or splines 56 do not extend all the way to the surface 58 which contains a central hole or opening 60 to permit the passage therethrough of an extension of the shaft 18. The splines extend only to a shoulder surface 62, which can be seen in FIGS. 1 and 6. Thus, the ported cap member 6, rotatable valve member and syringe member 2 are generally coaxially arranged along an axis extending lengthwise of shaft 18.

Referring now to the rotatable valve member 4, which is shown in greater detail in FIGS. 7-9, there is shown in FIG. 7 a view of the rotatable valve member 4 from its top, i.e., its face which is towards the ported cap member 6 in the device as assembled. In this view, it can be seen that there is, immediately interiorly adjacent to the exterior rim 63, the groove 24 for receiving the rim 26 of the ported cap member 6. Immediately interiorly adjacent to that, there is a shoulder 64, which provides a seat for the O-ring seal 36, as can be seen from FIG. 1. Immediately interiorly adjacent to the shoulder 64, there is a collar-like member 66 which forms the outside of fluid flow compartments 68, 70, and 72 and a fluid blockage segment 74. The compartments 68, 70, and 72, and segment 74 (defined as area 30 in FIG. 1) are interiorly bounded by another collar member 76, and having a shoulder 78 which provides a seat for the O-ring 38, arranged around the central opening 28 for the passage of the shaft 18. Collar-like members 66 and 76 extend into sealing engagement with gasket 53 in the cap member.

It will be seen that the compartment 68 extends around the central shaft to such an extent as to permit two of the ports of the ported cap member 6 to be in fluid communication with it, thereby connecting the lines attached to them to each other. Immediately adjacent to the compartment 68 is the compartment 70, which is open to permit the passage of fluid from the face which is toward the ported cap 6 to the compartment 32 which is towards the syringe assembly 2. Diametrically opposite compartment 70 is the fluid blockage segment 74. The rotatable valve member 4 fits down upon the syringe member 2 so that its surfaces 82 and 84, shown in FIG. 9, can freely rotate across opening 16 in the syringe member 2. In the device in its assembled position, the O-ring seal 38 bears upon the face 14 of the syringe member 2, so as to leave a space for liquid within the syringe member 2 to communicate to the compartment 70. The interior syringe assembly can be shut off by positioning the rotatable valve member 4 such that the top of the open compartment 70 is aligned not with one of the port holes 42, 44, 46, or 48, but rather with one of the parts of the surface 52 in between them.

The compartment 72 is in all respects similar to the compartment 68, extending peripherally about the central opening 28. The fluid blockage segment 74 has an upper surface which is, when the device is assembled, substantially coincident with the surface 52 of the ported cap member 6.

Referring now more particularly to FIGS. 8 and 9, it can be seen that when the rotatable valve member is viewed from the side towards the syringe member 2, there is an exterior rim 92, which is preferably provided with corrugations 94, for improved ability to manipulate the valve member 4 by hand. The interior face portion of the rotatable valve member facing toward the syringe member 2 has, as indicated in FIG. 9, a configuration such that there is an annular rim 96 adapted to fit snugly about the exterior of the syringe member 2 in the region designated 98 (FIG. 1). Interiorly of portion 96 is a shoulder 100 which provides a seat for the O-ring seal 34.

Although most of the exterior of the syringe assembly 2 has a configuration as shown in the left in FIG. 1 there is preferably provided, in accordance with the embodiment of the invention which is shown in these figures, a nub or protuberance 104 which projects from the exterior of the syringe member 2. Pairs of nubs or protuberances 108, 110, 112, and 114, as shown in FIGS. 8 and 9, extend from the interior of rim 96 of the rotatable valve member 4. The rotatable valve member 4 is thus securely but yieldingly held within a desired rotational position with respect to the rest of the apparatus, when the nub or protuberance 104 is between a desired one of the pairs of nubs or protuberances 108, 110, 112, or 114. It is preferred to provide that an audible click can be heard when the protuberance 104 passes any one of the protuberances 108, 110, 112 and 114.

As is indicated in the FIGS. 9A–9D, when the above-mentioned nub or protuberance 104 is within one or another of the various pairs of nubs or protuberances 108, 110, 112, and 114, then the syringe apparatus when employed as a urological device, will operate in one or another of four modes, namely, (1) fill, (2) irrigate, (3) drain, and (4) continuous. Those skilled in the art will understand that "fill" refers to the operation of withdrawing the plunger 10, and thereby causing a liquid to fill the interior of the syringe assembly 2 through port 44, compartment 70 and hole 16. In this position, the word "FILL" and its associated arrow comprising indicium 116 shown in FIG. 9A, are brought into alignment with arrow 22 (FIG. 3).

When the rotatable valve member 4 has been rotated so that the indicium 118, reading "IRRIG." and its associated arrow, is brought into alignment with the arrow 22, then the various compartments 68, 70, and 72 of the rotatable valve member 4 will be so positioned that there will take place, when the plunger 10 is activated, an appropriate irrigation action. This will mean that the compartment 70 of the rotatable valve member 4 is in communication with the port 46 which connects to a catheter extending to the bladder. Irrigation involves operating the plunger 10 to effect the introduction of fluid into the patient and the subsequent withdrawal of the plunger 10 to effect return of fluid into the syringe.

When the rotatable valve member 4 has been rotated so that the indicium 120, reading "DRAIN." and its associated arrow shown in FIG. 9C, is brought into alignment with the arrow 22, then the various compartments 68, 70, and 72 of the rotatable valve member 4 will be so positioned that there will take place, when the plunger 10 is activated, a discharge of fluid from the syringe. This will mean that the compartment 70 of the rotatable valve member 4 is in communication with port 48 which connects to a drain line.

When the rotatable valve member 4 has been rotated so that the indicium 122 reading "CONT." and its associated arrow shown in FIG. 9D, is brought into alignment with arrow 22, then compartment 68 is suitably located so that ports 42 and 44 are in fluid communication. Ports 46 and 48 are in simultaneous fluid communication by way of compartment 72. There is then obtained the effect of a continuous introduction of liquid into the system and the simultaneous drainage of fluid from the system.

To secure the ported cap member 6, the valve member and the syringe assembly 2 together there may be provided suitable means such as a nut threadedly engaged with a portion of the shaft 18 which extends through opening 60 of the cap. Alternatively, after the device is assembled, the part of the shaft which is remote from the syringe may be heat-deformed or otherwise suitably reshaped in order to provide an shoulder which serves to keep the parts together.

Although the invention has been shown in connection with a certain specific embodiment, it will be readily apparent to those skilled in the art that various changes in form and arrangement of parts may be made to suit requirements without departing from the spirit and scope of the invention.

I claim as my invention:

1. An assembly for introducing fluid into and removing liquid from a cavity, chamber or organ of the body of a biological being, said assembly including a container having a central axis, a ported cap member having ports adapted to be connected to means for conveying fluid into and removing fluid from said biological being, a rotatable valve member located between said container and said ported cap member in a fluid sealed manner with both said container and said ported cap member whereby relative rotation of said rotatable valve member about a rotational axis oriented generally the same as said central axis between said container and ported cap member may be effected in a fluid tight sealed manner, said rotatable valve member including a rim portion having a central axis generally parallel to said rotational axis of the valve member and extends along a portion of said container to seal said valve to said container, and, means for interfitting said ported cap member in a fixed manner with said container.

2. The assembly according to claim 1, wherein said rotatable valve member includes interior means for permitting communication of fluid between said container and at least one of the ports of said ported cap member, said interior means further permitting communication of fluid between ports of said ported cap member.

3. The assembly according to claim 1, further including indicia for indicating when said rotatable valve member is in a position such that a predetermined desired operating mode of said valve member is achieved.

4. The assembly according to claim 1, further including yielding and detenting means for yieldably indicating any one of a plurality of selectively operable positions of said rotatable valve member relative to both said container and said ported cap member.

5. The assembly according to claim 1, wherein said container comprises a syringe assembly.

6. The assembly according to claim 1, wherein said rotatable valve member includes means for forming a plurality of compartments, at least one of said compartments only interconnecting parts of said ported cap and another of said compartments interconnecting said container and said ported cap.

7. The assembly according to claim 1, wherein said means for interfitting include interfitting projections and slots for preventing relative rotation between said container and said ported cap.

8. The assembly according to claim 1, wherein said valve member and said container are nested one within the other and the valve and ported cap are nested one within the other.

9. The assembly according to claim 8 further including means for sealing interfitting surfaces of said ported cap and said rotatable valve member.

10. The assembly according to claim 8 further including means for sealing interfitting surfaces of said valve member and said container.

11. The assembly according to claim 1 wherein said means for interfitting include an extended part of said container about which said rotatable valve can rotate.

12. The assembly according to claim 11, wherein said extended part includes an enlarged portion to fasten said ported cap to said container.

13. The assembly according to claim 11, wherein said extended part is configured so as to fasten said ported cap to said container.

14. The assembly according to claim 11, wherein said extended part provides a surface for threadedly receiving a fastener.

15. The assembly according to claim 1 wherein said ported cap includes an internally projecting collar forming a bearing surface to support said rotatable valve member.

16. The assembly according to claim 15 wherein said ported cap includes an annular rim rotatably and sealably received in said valve member.

17. The assembly according to claim 1 wherein said means effects generally axial alignment of said ported cap and said container.

18. The assembly according to claim 17 wherein said rotatable valve member can rotate about an axis extending lengthwise through said container.

19. The assembly according to claim 1 wherein said container includes cylindrical end surfaces and wherein said means includes a support surface for coaxial rotation of said rotatable valve member about at least one of said cylindrical end surfaces.

20. An assembly for introducing fluid into and removing fluid from a cavity, chamber of organ of the body of a biological being, said assembly including a container having an extended part supported thereby, a ported cap member having ports adapted to be connected to means for conveying fluid into and removing fluid from said biological being, said ported cap member being supported by said extended part, and a rotatable valve member having an axis of rotation oriented generally the same as the longitudinal axis of said container, said rotatable valve member being located between the container and said ported cap member in a fluid sealed relation with said ported cap member, said rotatable valve member including a rim portion extending along a portion of the container said rim portion having a central axis oriented generally the same as the rotational axis of the valve member to form a seal with said container, said ported cap member and said container being non-rotatably interconnected by said extended part.

21. An assembly including a container having a central axis, a ported cap member having ports adapted to be connected to means for conveying fluid material, a rotatable valve member rotatable about an axis oriented generally the same as said central axis between said container and said ported cap member sealed in a fluid tight manner with both said container and said ported member, means for interfitting said ported cap member sealed in a fluid tight manner with both said container and said ported member, means for interfitting said ported cap member in a fixed manner with said container, and yielding and detenting means for yieldably indicating any one of a plurality of selectively operable positions of said rotatable valve member relative to both said container and said ported cap member, said yielding and detenting means include protuberances on each of said container and said rotatable valve to tactilely indicate a particular relative position between said rotatable valve and said container.

22. The assembly according to claim 21, wherein said protuberances on the container and the rotatable valve member produce an audible click as one protuberance passes another by rotation of the valve member.

23. An assembly including a container having a central axis, a ported cap member having ports adapted to be connected to means for conveying fluid material, a rotatable valve member between said container and said ported cap member sealed in a fluid tight manner with both said container and said ported cap member, said ported cap member including an internally projecting collar forming a bearing surface to support said rotatable valve member, said rotatable valve member including a rim portion having a central axis oriented generally the same as the rotational axis of said rotatable valve member, said rotational axis extended generally parallel to the central axis of said container, said rim portion extending along a portion of said container and rotatably sealed with said container, and, means for interfitting said ported cap member in a fixed manner with said container.

* * * * *